(12) United States Patent
Koser et al.

(10) Patent No.: US 6,624,333 B1
(45) Date of Patent: Sep. 23, 2003

(54) METHOD FOR PRODUCING BISPHENOL ALCOXYLATES

(75) Inventors: Stefan Koser, Ludwigshafen (DE); Klaus Mundinger, Limburgerhof (DE); Wolfgang Kasel, Nussloch (DE); Arend Jouke Kingma, Ludwigshafen (DE); Toni Dockner, Meckenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,814

(22) PCT Filed: Jun. 21, 2000

(86) PCT No.: PCT/EP00/05753

§ 371 (c)(1), (2), (4) Date: Dec. 21, 2001

(87) PCT Pub. No.: WO00/78698

PCT Pub. Date: Dec. 28, 2000

(30) Foreign Application Priority Data

Jun. 22, 1999 (DE) .......................... 199 28 549
Feb. 10, 2000 (DE) .......................... 100 05 792

(51) Int. Cl.$^7$ ............................................. C07C 41/03
(52) U.S. Cl. ..................................................... 568/609
(58) Field of Search ........................................ 568/609

(56) References Cited

U.S. PATENT DOCUMENTS

| 4,846,996 A | | 7/1989 | Carroll et al. .......... 252/182.16 |
| 5,059,723 A | * | 10/1991 | Dressler ...................... 568/45 |
| 5,342,903 A | * | 8/1994 | Wolleb et al. .............. 525/407 |

FOREIGN PATENT DOCUMENTS

| EP | 0 466 319 | 1/1992 | ........... C07C/43/23 |

OTHER PUBLICATIONS

Z.–C. Sheng: "Study on unsaturated polyester resins of the bisphenol A type. Part I. Syntheses of D–33 monomer and 323 resin.", Chemical Abstracts, vol. 94, No. 8, pp. 48 and 92, Feb. 23, 1981.

Database WPI, Section Ch, Week 8603, Derwent Publications Ltd., London, GB; AN 1986–018517, JP60243036A, 19851203.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

A process for preparing bisphenol alkoxylates comprises reacting at least one bisphenol with alkylene oxide in the presence of a phosphine catalyst which is essentially free of alkali metal hydroxide.

17 Claims, No Drawings

METHOD FOR PRODUCING BISPHENOL ALCOXYLATES

The present invention relates to a process for preparing bisphenol alkoxylates, in particular bisphenol A alkoxylates. In addition the invention relates to the use of catalysts employed for this purpose.

Bisphenol alkoxylates are used for a wide variety of applications, for example for the synthesis of polyester resins (JP 59012-934-A) and polyurethanes (JP 59197-417-A).

Bisphenol alkoxylates, in particular bisphenol A alkoxylates, are prepared, as is known to those skilled in the art, from bisphenol A by reaction with an alkylene oxide, e.g. ethylene oxide, propylene oxide or butylene oxide (JP 60243-036-A), in the presence of a catalyst. Catalysts used are, in particular, alkali metal hydroxides such as sodium hydroxide, potassium hydroxide or tertiary amines (see the above mentioned JP publications and also Shanghai Inst. Chem. Technol., Shanghai in Chemical Abstracts 94:48110).

The alkoxylation reaction can lead to different addition products. The known catalysts, for instance, lead to a product in which the addition products have a relatively broad molar mass distribution.

If a high reaction selectivity is desired, solvents are sometimes used in order to influence the selectivity of the alkylene oxide addition onto bisphenol A in the desired direction (U.S. Pat. No. 4,846,996). However, this measure leads to a reduction in the space-time yield, since the solvent used has to be removed again after the reaction is complete.

Another possible way of solving the problem is to allow the reaction of a phenol with an alkylene oxide to proceed in the presence of phosphonium halides as catalysts, in the presence or absence of a solvent.(JP AS 654/75; DE-A 2 157 455).

A further measure to obtain a bisphenol A addition product having a narrow molar mass distribution is crystallization of the product. However, this step likewise reduces the space-time yield and additionally leads to reduced yields.

Sheng Zhicong et al. [Shang-hai Hua Kung Hsueh Yuan Hsueh Pao 1980, 48 (1), 92] describe studies on the reaction of propylene oxide with bisphenol A. It is stated that the preferred catalyst is NaOH and that the amount of catalyst can be reduced if concomitant use is made of a Lewis base such as triethylamine or triphenylphosphine (i.e. the Lewis base is used as cocatalyst). However, further information which would enable a person skilled in the art to carry out the reaction is lacking in this publication. In addition, there is the undesirable effect that the catalyst loses its activity toward the end of the reaction and the bisphenol A monopropoxylate content is increased as a consequence.

A low selectivity is therefore to be expected when using other alkylene oxides, too. This applies especially to ethylene oxide, since ethylene oxide is significantly more reactive than propylene oxide. A person skilled in the art would therefore expect the formation of multiply ethoxylated products and thus a broader molar mass distribution.

It is an object of the present invention to provide a process for preparing bisphenol alkoxylates, in particular bisphenol A alkoxylates, which gives, dialkoxylated products with high selectivity and in which, in particular, uncontrolled multiple alkoxylation is avoided.

We have found that this object is achieved by a process for preparing bisphenol alkoxylates, which comprises reacting at least one bisphenol with an alkylene oxide in the presence of a phosphine catalyst.

In a preferred embodiment, the process of the invention is carried out in the absence of solvents, i.e. a mixture, in particular a melt, of the bisphenol and the phosphine catalyst is prepared first and the reaction with the alkylene oxide is then carried out. However, the reaction can also be carried out in the presence of an inert solvent. Solvents which can be used are, for example, hydrocarbons such as toluene or xylene and ketones such as methyl ethyl ketone or diethyl ketone.

Preferred alkylene oxides are $C_2$–$C_4$-alkylene oxides, in particular ethylene oxide, propylene oxide and 1,2-butylene oxide and mixtures thereof, with particular preference being given to ethylene oxide. Styrene oxide is also suitable.

In the process of the present invention, the catalysts used are materials belonging to the class of substituted phosphines. These are preferably selected from the group consisting of substituted phosphines of the formula (I) below:

where $R^1$, $R^2$ and $R^3$ are aryl radicals of the formula (II) below,

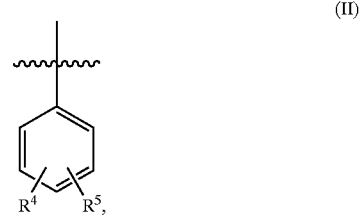

where $R^4$ and/or $R^5$ can be identical or different and are selected from among H, $C_1$–$C_3$-alkyl groups, $C_1$–$C_3$-alkoxy groups, carboxyl groups and sulfonic acid groups.

Preferred catalysts of the above formula (I) are phosphines in which at least two of the radicals $R^1$, $R^2$ and $R^3$ are identical. Particular preference is given to phosphines in which the substituents $R^1$, $R^2$ and $R^3$ are identical.

Very particular preference is given to substituted phosphines in which the radicals $R^1$, $R^2$, $R^3$ are phenyl, o-tolyl, m-tolyl or p-tolyl groups. Such particularly preferred phosphine catalysts include, for example, tri-para-tolylphosphine, tri-ortho-tolylphosphine, tris(3-sulfophenyl) phosphine and its salts, in particular the trisodium salt, and particularly preferably triphenylphosphine.

The phosphine catalyst can also be employed together with a tri-$C_1$–$C_{12}$-alkylamine as cocatalyst. The amount of cocatalyst can be up to 35% by weight, based on the total weight of the catalyst. Examples of cocatalysts are triethylamine, tri-n-propylamine, tri-n-butylamine, etc.

The phosphine catalysts described are particularly suitable for the reaction of bisphenols of the formula

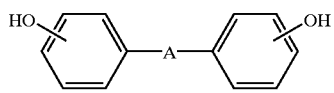

where A is a straight-chain or branched $C_1$–$C_4$-alkylene group,

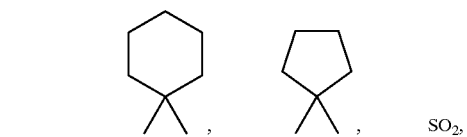, $SO_2$,

—$CH_2OCH_2$—, —O— or —S—. Preferably, A is

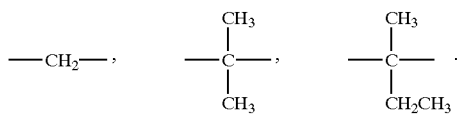

The OH groups are preferably in the 4 and 4' positions.

Particular preference is given to bisphenol A (2,2-bis(4-hydroxyphenyl)propane), bisphenol B (2,2-bis(4-hydroxyphenyl)butane), bisphenol C (1,4-bis(4-hydroxyphenyl)cyclohexane) and bisphenol F (2,2'-methylenediphenol).

The alkoxylation products obtained are thus bisphenol alkoxylates of the formula

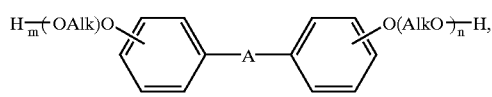

where A is as defined above, m and n are 0 or 1, with m and n being able to be identical or different but not both 0, and Alk is a $C_2$–$C_4$-alkylene group or $C_6H_5$—CH—$CH_2$—, in particular —$CH_2$-$CH_2$—, The process of the invention can be illustrated by means of scheme 1 below using the reaction of bisphenol A with ethylene oxide as an example.

Scheme 1:

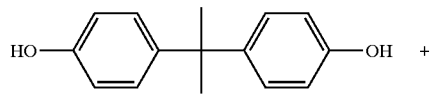

Scheme 2:

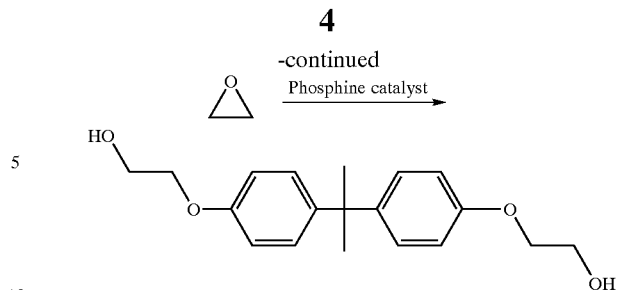

A very particular advantage of the process of the invention is the high reaction selectivity, in particular with avoidance of the use of a solvent.

The process of the invention is preferably carried out at from 90° C. to 180° C. The pressure is generally in the range from 1 to 50 bar, preferably from 1 to 20 bar, in particular from 2 to 15 bar.

The catalyst is generally used in an amount of from 0.01 to 5% by weight, preferably from 0.1 to 5% by weight, in particular from 0.1 to 2% by weight, based on bisphenol used. In general, the reaction is carried out essentially in the absence of water, i.e. the water content of the reaction mixture is ≦1% by weight, based on the weight of the reaction mixture.

The amount of alkylene oxide used depends on the product desired. In general, it is used in an amount of from about 1.9 to 2.5 equivalents, based on bisphenol. After the reaction is complete, the alkylene oxide is removed in a customary manner, e.g. by application of a vacuum.

In a preferred embodiment of the process of the present invention, the bisphenol dialkoxylates obtained in accordance with scheme 1 above are converted into the corresponding more highly alkoxylated bisphenol alkoxylates in a subsequent reaction with an alkylene oxide (ethylene oxide, propylene oxide, butylene oxide or styrene oxide). As catalyst, use is made here of an alkali metal hydroxide such as NaOH, KOH, CsOH or LiOH, an alkaline earth metal hydroxide such as magnesium hydroxide or calcium hydroxide or a DCM catalyst as described, for example, in WO 99/16775. The subsequent reaction is illustrated in scheme 2 below using KOH as catalyst and ethylene oxide:

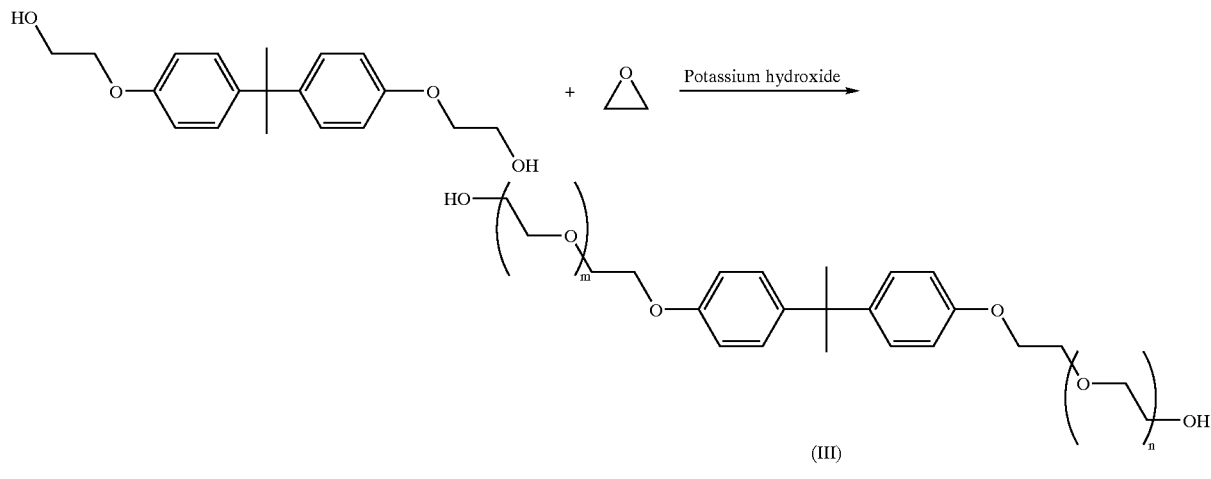

(III)

m, n, = 0, 1, 2, 3

In this scheme, m and n can be identical or different and be from 0 to 20, in particular 0, 1, 2 or 3, with m and n not both being able to be 0. It has surprisingly been found that the more highly alkoxylated compounds can also be obtained in purer form than is obtained according to the prior art. Preference is given to syntheses which lead to compounds with m=n=1.

The above-described subsequent reaction is carried out under essentially the same conditions as the reaction of the bisphenol with the alkylene oxide.

Bisphenol ethoxylates which can be synthesized by means of the process of the present invention are shown below by way of example:

a)

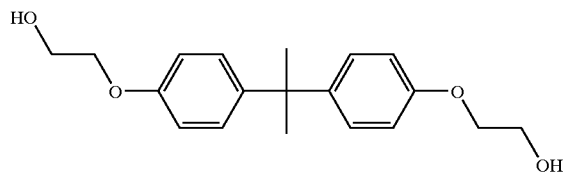

b)

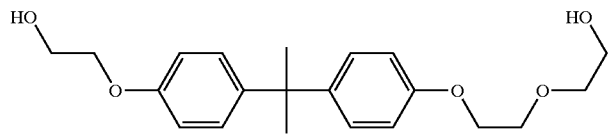

c)

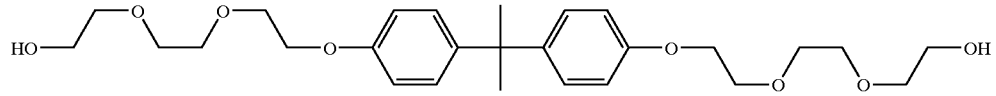

d)

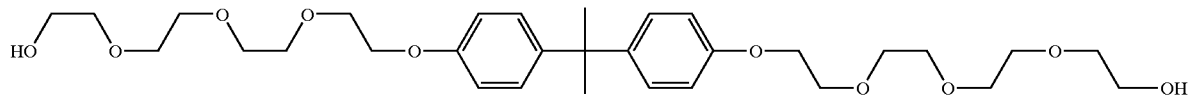

The invention is illustrated by the following example.

EXAMPLE 1

548 g of bisphenol A and 3.15 g of triphenylphosphine were melted together. 215.8 g of ethylene oxide were subsequently added at from 120 to 170° C. over a period of 2.9 hours. After the ethylene oxide had been fed in, the mixture was stirred within the temperature range indicated until the pressure was constant. After application of a vacuum for from about 1 to 2 hours, the product (765 g) was drained from the reactor. According to GC analysis, the product contained 92.7% of the compound of the formula a) above.

We claim:

1. A process for preparing bisphenol alkoxylates, which comprises reacting at least one bisphenol with an alkylene oxide in the presence of a substituted phosphine catalyst, the catalyst being free of alkali metal hydroxide, wherein the substituted phosphine catalyst is selected from the group consisting of substituted phosphines of the formula (I) below:

where $R^1$, $R^2$ and $R^3$ are aryl radicals of the formula (II) below,

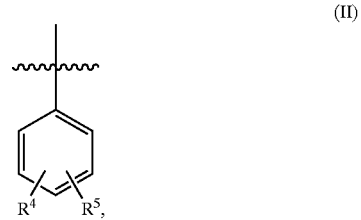

where $R^4$ and $R^5$ are identical or different and are selected from the group consisting H, $C_1$–$C_3$-alkyl groups, $C_1$–$C_3$-alkoxy groups, —COOM groups and $SO_3M$ groups, where M is H or an alkali metal.

2. A process as claimed in claim 1, wherein the reaction is carried out in the melt.

3. A process as claimed in claim 1, wherein in the substituted phosphine catalysts of the formula (I), the radicals $R^1$, $R^2$ and $R^3$ are identical.

4. A process as claimed in claim 1, wherein the radicals $R^1$, $R^2$ and $R^3$ are independently selected from the group consisting of phenyl, o-tolyl, m-tolyl, p-tolyl, m-sulfophenyl and sodium m-sulfophenyl.

5. A process as claimed in claim 4, wherein the substituted phosphine catalyst is triphenylphosphine, tri-o-tolylphosphine or tris(3-sulfophenyl)phosphine or a salt thereof.

6. A process as claimed in claim 1 wherein the bisphenol is of the formula

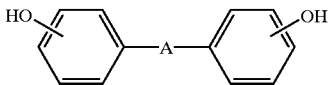

where A is a straight-chain or branched $C_1$–$C_4$-alkylene group,

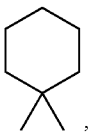 , 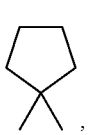 , $SO_2$,

—$CH_2OCH_2$—, —O— or —S—.

7. A process for preparing a bisphenol multiple alkoxylate comprising preparing a bisphenol di-monoalkoxylate first by reacting at least one bisphenol with an alkylene oxide in the presence of a substituted phosphine catalyst, the catalyst being free of alkali metal hydroxide, to produce the bisphenol di-monoalkoxylate, and then reacting the bisphenol di-monoalkoxylate with an alkylene oxide to form the multiple alkoxylate of the formula (II) below

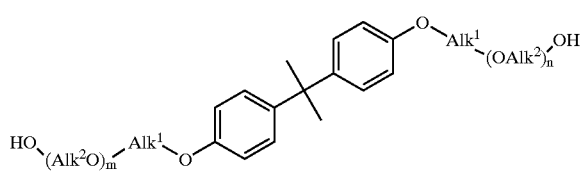

where m and n are identical or different and are 0, 1, 2 or 3, with m and n not both being able to be 0, and $Alk^1$ and $Alk^2$, which are can be identical or different, are $C_2$–$C_4$-alkylene or Ph—CH—$CH_2$— or combinations thereof.

8. A process as claimed in claim 1, wherein the alkylene oxide is ethylene oxide.

9. A process as claimed in claim 4, wherein the alkylene oxide is ethylene oxide.

10. A process as claimed in claim 9, wherein the bisphenol is bisphenol A and the substituted phosphine catalyst is triphenyl phosphine.

11. A process as claimed in claim 1, wherein a tri-$C_1$–$C_{12}$-alkylamine cocatalyst is employed with the phosphine catalyst in an amount up to 35% by weight, based on the total weight of the catalyst.

12. A process as claimed in claim 7, wherein the substituted phosphine catalyst is selected from the group consisting of substituted phosphines of the formula (I) below:

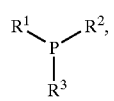

where $R^1$, $R^2$ and $R^3$ are aryl radicals of the formula (II) below,

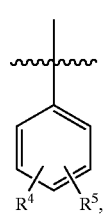

where $R^4$ and $R^5$ are identical or different and are selected from the group consisting H, $C_1$–$C_3$-alkyl groups, $C_1$–$C_3$-alkoxy groups, —COOM groups and $SO_3M$ groups, where M is H or an alkali metal.

13. A process as claimed in claim 12, wherein in the substituted phosphine catalysts of the formula (I), the radicals $R^1$, $R^2$ and $R^3$ are identical.

14. A process as claimed in claim 13, wherein the radicals $R^1$, $R^2$ and $R^3$ are independently selected from the group consisting of phenyl, o-tolyl, m-tolyl, p-tolyl, m-sulfophenyl and sodium m-sulfophenyl.

15. A process as claimed in claim 14, wherein the substituted phosphine catalyst is triphenylphosphine, tri-o-tolylphosphine or tris(3-sulfophenyl)phosphine or a salt thereof.

16. A process as claimed in claim 15 wherein the bisphenol is of the formula

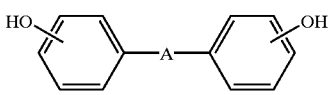

where A is a straight-chain or branched $C_1$–$C_4$-alkylene group,

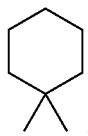 , 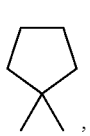 , $SO_2$,

—$CH_2OCH_2$—, —O— or —S—.

17. A process according to claim 16, wherein the alkylene oxide is ethylene oxide.

* * * * *